(12) United States Patent
Mallires et al.

(10) Patent No.: US 10,867,720 B2
(45) Date of Patent: Dec. 15, 2020

(54) IMPREGNATION OF A NON-CONDUCTIVE MATERIAL WITH AN INTRINSICALLY CONDUCTIVE POLYMER

(71) Applicant: Heraeus Medical Components LLC, St. Paul, MN (US)

(72) Inventors: Kyle Mallires, St. Paul, MN (US); Jeffrey L. Hendricks, St. Paul, MN (US); Sarah Richardson-Burns, St. Paul, MN (US); Omar Amirana, St. Paul, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 74 days.

(21) Appl. No.: 16/139,397

(22) Filed: Sep. 24, 2018

(65) Prior Publication Data

US 2019/0131028 A1 May 2, 2019

Related U.S. Application Data

(63) Continuation of application No. 14/891,967, filed as application No. PCT/US2014/038630 on May 19, 2014, now Pat. No. 10,109,386.

(60) Provisional application No. 61/824,404, filed on May 17, 2013.

(51) Int. Cl.

| H01B 1/12 | (2006.01) |
|---|---|
| A61L 27/48 | (2006.01) |
| A61L 27/50 | (2006.01) |
| H01B 1/24 | (2006.01) |
| B05D 1/18 | (2006.01) |
| B05D 3/10 | (2006.01) |
| C09D 5/24 | (2006.01) |
| C09D 175/04 | (2006.01) |
| C09D 181/02 | (2006.01) |
| C25B 3/00 | (2006.01) |
| C25D 9/02 | (2006.01) |
| H01B 13/30 | (2006.01) |
| C08L 65/00 | (2006.01) |

(52) U.S. Cl.
CPC .............. *H01B 1/127* (2013.01); *A61L 27/48* (2013.01); *A61L 27/50* (2013.01); *B05D 1/185* (2013.01); *B05D 3/108* (2013.01); *C09D 5/24* (2013.01); *C09D 175/04* (2013.01); *C09D 181/02* (2013.01); *C25B 3/00* (2013.01); *C25D 9/02* (2013.01); *H01B 1/24* (2013.01); *H01B 13/30* (2013.01); *C08G 2261/1424* (2013.01); *C08G 2261/18* (2013.01); *C08G 2261/3223* (2013.01); *C08G 2261/43* (2013.01); *C08G 2261/44* (2013.01); *C08G 2261/51* (2013.01); *C08G 2261/792* (2013.01); *C08L 65/00* (2013.01)

(58) Field of Classification Search
CPC .......... C08L 65/00; C08L 75/04; A61L 27/48; A61L 27/50; B05D 1/185; B05D 3/108; C08G 2261/1424; C08G 2261/18; C08G 2261/3223; C08G 2261/43; C08G 2261/44; C08G 2261/51; C08G 2261/792; C09D 175/04; C09D 181/02; C09D 5/24; C25B 3/00; C25D 9/02; H01B 13/30; H01B 1/127; H01B 1/24
See application file for complete search history.

(56) References Cited

U.S. PATENT DOCUMENTS

| 4,582,575 | A | 4/1986 | Warren et al. |
| 4,604,427 | A * | 8/1986 | Roberts ................ C08G 61/124 |
| | | | 252/500 |
| 5,385,956 | A | 1/1995 | Schellekens et al. |
| 5,508,348 | A | 4/1996 | Ruckenstein et al. |
| 5,908,705 | A | 6/1999 | Nguyen et al. |
| 5,972,499 | A | 10/1999 | Rodriguez et al. |
| 6,132,752 | A | 10/2000 | Pickett et al. |
| 6,156,235 | A * | 12/2000 | Bessette ..................... C08J 9/42 |
| | | | 252/511 |
| 7,708,908 | B2 | 5/2010 | Kim et al. |
| 8,005,526 | B2 | 8/2011 | Martin et al. |
| 8,343,212 | B2 | 1/2013 | Pickett et al. |
| 8,380,306 | B2 | 2/2013 | Pickett |
| 8,577,476 | B2 | 11/2013 | Hendricks et al. |
| 8,936,794 | B2 | 1/2015 | Martin et al. |
| 9,050,454 | B2 | 6/2015 | Hendricks et al. |
| 9,084,546 | B2 | 7/2015 | Richardson-Burns et al. |
| 2005/0202251 | A1 | 9/2005 | Elschner et al. |
| 2007/0278453 | A1 | 12/2007 | Zahn et al. |
| 2008/0142762 | A1 | 6/2008 | Ni et al. |
| 2009/0297909 | A1 | 12/2009 | Yamamoto et al. |
| 2010/0312331 | A1 | 12/2010 | Pickett et al. |
| 2011/0257504 | A1 | 10/2011 | Hendricks et al. |
| 2011/0315204 | A1 | 12/2011 | Gleason et al. |
| 2012/0208086 | A1 | 8/2012 | Plieth et al. |
| 2014/0277318 | A1* | 9/2014 | Richardson-Burns ....................... |
| | | | C09D 5/4407 |
| | | | 607/116 |
| 2015/0303477 | A1 | 10/2015 | Lovenich et al. |
| 2016/0177109 | A1 | 6/2016 | Hendricks et al. |

FOREIGN PATENT DOCUMENTS

| JP | H03-215520 A | 1/1990 |
| JP | 2002-220484 A | 8/2002 |

(Continued)

OTHER PUBLICATIONS

Gok, A., et al., "Synthesis and Characterization of Polythiophenes Prepared in the Presence of Surfactants," Synthetic Metals, 2007, pp. 23-29, vol. 157.

(Continued)

*Primary Examiner* — Mark Kopec
*Assistant Examiner* — Jaison P Thomas
(74) *Attorney, Agent, or Firm* — Stradley Ronon Stevens & Young, LLP

(57) ABSTRACT

Composite materials are made by impregnating a non-conductive material with a conducting monomer to form a monomer-impregnated non-conductive material, and polymerizing the monomer-impregnated non-conductive material to form the composite material. The composite materials are used in medical devices and implants.

15 Claims, No Drawings

(56) References Cited

FOREIGN PATENT DOCUMENTS

| JP | 2010-106245 A | 5/2010 |
|----|---------------|--------|
| JP | 2012-097132 A | 5/2012 |
| WO | 2010/058108 A1 | 5/2010 |
| WO | 2013/135363 A1 | 9/2013 |
| WO | 2014/154360 A2 | 10/2014 |
| WO | 2015/031265 A1 | 3/2015 |

OTHER PUBLICATIONS

International Search Report issued in International PCT Application No. PCT/US2014/038630, dated Sep. 17, 2014, 6 pages.
Written Opinion issued in International PCT Application No. PCT/US2014/038630, dated Sep. 17, 2014, 9 pages.
International Preliminary Report on Patentability issued in International PCT Application No. PCT/US2014/038630, dated Nov. 26, 2015, 11 pages.
Supplementary Partial European Search Report issued for EP 14797260.8, dated Nov. 30, 2016, 7 pages.
Sessolo, M., et al., "Easy-to-Fabricate Conducting Polymer Microelectrode Arrays," 2013, Adv Mater, 1-5, wileyonlinelibrary.com.

\* cited by examiner

IMPREGNATION OF A NON-CONDUCTIVE MATERIAL WITH AN INTRINSICALLY CONDUCTIVE POLYMER

CROSS-REFERENCE TO RELATED APPLICATION

This application is a continuation of U.S. patent application Ser. No. 14/891,967, filed Nov. 17, 2015, which is a U.S. National Stage of PCT/US2014/038630 filed May 19, 2014, which claims the benefit of U.S. Provisional Patent Application Ser. No. 61/824,404, filed May 17, 2013, the entire content of which are incorporated herein by reference.

FIELD OF THE INVENTION

The present invention generally relates to chemical processes and methods for the loading of an electrically insulating material with an intrinsically electrically conductive polymer, thereby imparting the existing material with electrical conductivity.

BACKGROUND OF THE INVENTION

Although the vast majority of plastics are electrically insulating, there is frequently a need for the preparation of plastics having electrical conductivity. Applications of electrically conductive plastics can include anti-static discharge protection, electromagnetic interference shielding, electrode materials, electrically conducting wires or traces, and semiconductor devices (OLEDs, photovoltaics, transistors).

Difficulties arise when a manufacturer wants to incorporate electrical conductivity into a plastic component that is already being manufactured in significant quantities. To add conductivity, manufacturers are faced with the undesirable prospect of switching to a new raw material having the desired electrical properties, and then reconfiguring their processes to account for the changed mechanical and/or chemical properties associated with the new raw material.

There is therefore a need in the art for a method which allows manufacturers to form, mold, shape, machine, cast, and/or extrude plastics without changing their starting materials and manufacturing processes, and then impart electrical conductivity to these materials through the use of a non-destructive, post-process application.

SUMMARY OF THE INVENTION

In one aspect, the present invention is directed to a method of making a composite material, the method comprising the steps of: impregnating a non-conductive material with a conducting monomer to form a monomer-impregnated non-conductive material; and polymerizing the monomer-impregnated non-conductive material to form the composite material.

Another aspect of the present invention is directed to a composite material comprising a non-conductive material impregnated with a conducting polymer, the composite material being prepared by a process as described herein.

A further aspect of the present invention is directed to a composite material comprising a conducting polymer entrapped within a non-conductive material.

Another aspect of the present invention is directed to a method of promoting rapid or accelerated endothelial cell colonization and endothelialization, preventing thrombus formation on the surface of an implant, or promoting thrombus formation on the surface of an implant, or effecting a physiologic response from the biological environment in which it is placed or implanted comprising implanting an implant comprising a composite material as described herein.

DESCRIPTION OF THE INVENTION

It has been discovered that an electrically non-conductive material may be impregnated with an intrinsically conductive polymer (ICP) by in-situ polymerization. Advantageously, the processes and methods disclosed herein do not destroy or severely change the existing shape and material properties of the non-conductive starting material. Rather, the non-conductive starting material can be formed, machined, extruded, molded, shaped, cast, and/or modified before the in-situ polymerization begins. This allows manufacturers to form plastics into finished parts or products from familiar, readily available starting materials, and gain electrical conductivity through a non-destructive post-process application without changing their existing processes.

The processes and methods described herein can comprise at least two steps. In an initial step, the non-conductive starting material is impregnated with a conductive monomer. In a further step, the conductive monomer-impregnated material undergoes a polymerization step wherein the conductive monomer is polymerized in situ. The polymerization step may comprise chemical oxidative polymerization, electrochemical polymerization, or a combination thereof. The result is the formation of an electrically conductive composite material, wherein a conductive polymer is impregnated within the non-conducting starting material.

Alternatively, the processes and methods described herein can comprise a single step of impregnating the non-conductive material with a conductive monomer and polymerizing the conductive monomer by chemical oxidative or electrochemical polymerization or a combination thereof.

In an initial step of the chemical process, the non-conductive material is infused with an infusion medium comprising the conductive monomer. Generally, and as described in further detail below, the non-conductive material is exposed to an impregnation medium (also referred to herein as an infusion medium), which causes the non-conductive material to take-up the monomer by swelling or a similar infusion mechanism. The presence of swelling or a similar infusion mechanism may be generally recognized, for example, where the non-conductive material substrate exhibits an increase in mass following exposure to the infusion medium.

This swelling or infusion process consequently allows the conductive monomer to impregnate into, and disperse throughout, the non-conductive material. Advantageously, this process is non-destructive with regard to the non-conductive material, and can be performed on manufactured parts or products without changing the existing geometry.

Typically, the infusion medium is in the form of a liquid composition.

When the infusion medium is a liquid, the non-conductive material is typically soaked in the liquid infusion medium for about 15 minutes to about 250 hours, more typically from about 12 hours to about 48 hours, preferably from about 12 hours to about 36 hours, and more preferably for about 24 hours.

The impregnating step typically occurs at a temperature of from about 0° C. to about 120° C. Preferably, the impregnating step occurs at about 20° C. to 40° C. such as at room temperature (i.e., about 25° C.) to about 37° C.

Alternatively, the infusion medium may be in the form of a gas, vapor, and/or plasma. For example, some monomers exist as a gas at standard temperature and pressure (e.g., acetylene), and are more suited to a gas-phase impregnation step than a liquid-phase process as described above.

Typically, a gas-phase infusion step is initiated by placing the non-conducting material substrate into a sealed chamber, into which the conductive monomer is delivered either as a gas or a liquid. Pressures lower than atmospheric pressure are typically employed to make the insulating polymers more porous, so that they absorb more of the conductive monomer into their bulk.

Depending on the rate of conductive monomer diffusion and the thickness of the non-conductive material substrate, infusion of the gaseous conductive monomer typically takes from 15 minutes to 48 hours such as between 15 minutes and 12 hours.

Monomers that exist as a liquid in their pure state at room temperature and standard pressure (e.g., EDOT, pyrrole) can infuse into the material as a vapor. This technique is particularly useful for monomers having a high vapor pressure. Typically, the vapor pressure of a monomer may be increased by increasing the temperature thereof or decreasing the pressure of the sealed chamber. Increasing the vapor pressure in this manner is usually effective to achieve vapor-phase infusion of the monomer into the non-conductive material, provided that the temperature does not increase to a level that damages the material being infused or drives chemical reactions leading to degradation of the monomer species.

When the infusion medium is in the form of a liquid, gas, vapor and/or plasma, the infusion medium comprises from about 0.1 to 100% v/v of the conducting monomer and from 0 to about 99.9% v/v of the organic solvent, or preferably from about 50 to about 90% v/v of the conducting monomer and from about 10 to about 50% v/v of the organic solvent.

The conductivity of the final, conductive polymer-infused composite material may be tuned by adjusting the concentration of the conductive monomer in the infusion medium. For example, the electrical conductivity of the final composite material may be maximized by using high loading levels of the conductive monomer during the infusion step.

To prepare a final composite material with less than the maximum possible electrical conductivity, a solvent may be added to the infusion medium in order decrease the concentration of the monomer, which correspondingly decreases the amount of monomer absorbed into the non-conductive material. In addition, some solvents may alter the swelling properties of the material, relative to an infusion medium comprising only the conductive monomer. To the extent that a solvent increases (or reduces) the swelling of the non-conductive material, the material will absorb more (or less) monomer and, therefore, will exhibit a greater (or lesser) conductivity following polymerization. Decreasing the amount of conductive polymer impregnated in the final composite material by controlling conductive monomer infusion will aid in maintaining the mechanical properties of the non-conducting starting material.

A portion of the non-conductive material may be masked prior to the impregnating step.

In a further step of the chemical process, the conductive monomer-impregnated material may be exposed to an oxidizer.

When the conductive monomer-impregnated material is exposed to an oxidizer, the conductive monomer undergoes polymerization to form a conductive polymer. The resulting material may be referred to as a "composite material," wherein the conductive polymer is impregnated within and dispersed throughout the non-conducting starting material.

The composite material can be an interpenetrating polymer network.

Typically, the oxidation step is performed immediately following the infusion step described above.

The conductive monomer-impregnated material can be soaked in a liquid oxidation medium comprising the oxidizer.

The oxidation step may occur in the presence of agitation. Typically, the agitation comprises shaking or stirring.

The liquid oxidation medium can comprise from about 0.01 to about 20% v/v of an oxidizer and from about 80 to about 99.99% v/v of an organic solvent, or from about 0.01 to about 10% v/v of an oxidizer and from about 90 to about 99.99% v/v of an organic solvent.

The conductive monomer-impregnated material may be soaked in a liquid oxidation medium for about 15 seconds to about 72 hours, from about 4 hours to about 48 hours, from about 12 hours to about 36 hours, from about 12 to 24 hours, and more typically for about 12 hours to about 18 hours.

The conductive monomer-impregnated material may be oxidized by exposure to gas, vapor, or plasma comprising the oxidizer.

The oxidation step may be carried out at a temperature from about 0° C. to about 120° C., more typically from about 20° C. to about 60° C. The oxidation step may be carried out at an elevated temperature (e.g., a temperature greater than 25° C.). For example, the oxidation step may be carried out at a temperature of from about 30° C. to about 50° C., more typically from about 35° C. to about 45° C., and more typically at about 25° C. to about 37° C. Higher temperatures can be used to reduce reaction time. Lower temperatures can increase conductivity and retain mechanical properties.

In a further step of the chemical process, following exposure to the oxidizer, the composite material may optionally be rinsed to remove excess monomer, solvent, counterions, or other chemical species that may be present as a result of the steps described above.

The composite material may be rinsed with a rinsing medium comprising water, an organic solvent, or a combination thereof.

The composite material may be sonicated or agitated in the rinsing medium to facilitate removal of the undesirable excess chemical species. The conductive polymer-infused material may also be pressure washed with the rinsing medium.

Typically, the organic solvent has a high vapor pressure such that it completely evaporates off of the composite material. Additionally, the organic solvent should not cause the conducting polymer to swell excessively, which could lead to changes in the composite properties and consequently lower the conductivity.

Preferably, the organic solvent is a polar organic solvent. Polar organic solvents facilitate the removal of residual water from the composite material.

Electrochemical polymerization may be employed as a method of polymerizing the conductive monomer. The electrochemical polymerization may take place in addition to, or as an alternative to, the oxidative polymerization step described above.

For example, electrochemical polymerization can be used on the conductive monomer-impregnated material once a small amount of conductivity has been achieved through chemical polymerization initiated by contact with the oxidation medium.

Alternatively, electrochemical polymerization may be utilized to polymerize the conductive monomer-impregnated substrate immediately following the infusion step, and in the absence of any contact with an oxidation medium.

Impregnation of the non-conductive material or substrate and electrochemical polymerization can also occur in one step by exposing the non-conductive material to a medium containing a conductive monomer and counter-ions and polymerizing. For example, the non-conductive material can be immersed in a bath containing conductive monomer, solvent and counter-ions.

The electrochemical polymerization step is typically carried out inside a container or vessel containing at least two electrodes. More typically, the container or vessel comprises a working or sense electrode (WE); a counter or return electrode (CE) having approximately 10 fold greater surface area as compared to the WE, and which is preferably made of platinum, platinized titanium, or platinized niobium; and, optionally, a reference electrode (RE), which is preferably a KCl saturated Ag/AgCl or calomel reference electrode.

The electrochemical polymerization step may be carried out in a medium comprising a solvent (such as water or an organic solvent) and counter-ions. A non-limiting example of a typical medium for electrochemical polymerization comprises acetonitrile and lithium trifluoromethanesulfonate (counterion).

When impregnation and electrochemical polymerization occur in one step, a polymerization medium is used. The polymerization medium comprises a solvent (such as water or an organic solvent), counter-ions and a conducting monomer. A non-limiting example of a typical polymerization medium for electrochemical polymerization comprises acetonitrile, EDOT monomer and lithium trifluoromethanesulfonate (counterion). Non-limiting examples of suitable organic solvents and counterions are set forth in detail herein. A one step procedure may be preferred in instances where time or process constraints exist, or the non-conductive substrate is more amenable to a one step procedure.

A one step impregnation and electrochemical polymerization can be performed, for example, by preparing a polymerization medium by combining the solvent, counter-ions and optional components (e.g., oxidizer, dopant, etc.), then adding the conductive monomer. As soon as the monomer is combined into the medium, the polymerization medium is active and polymerization will occur. Thus, the non-conductive substrate is immersed in the polymerization medium before the conductive monomer is added to the medium or immediately after the conducting monomer is added. If an oxidizer is present, the chemical oxidative reaction proceeds as described above. After polymerization is complete, the samples may be rinsed as described above.

The electrochemical polymerization step is typically carried out at room temperature (from about 20° C. to about 40° C.). Optionally, the polymerization solution is gently agitated or stirred during the electrochemical polymerization step. Additionally, the pH of the polymerization solution is typically maintained within a range of from about 1 to about 10, preferably from about 2.5 to about 10, during the electrochemical polymerization step.

Electrical current between the working and counter electrode is typically applied at a density of from about 0.1 $mA/cm^2$ to about 10.0 $mA/cm^2$.

The electrochemical polymerization typically occurs for from about 1 minute to about 24 hours, preferably from about 15 minutes to about 12 hours, and more preferably from about 15 minutes to about 6 hours.

In another aspect, the methods can include melt and/or solution processing of the non-conductive material substrate (e.g., the material to be impregnated with the conductive monomer) prior to or during incorporation of the conducting polymer.

Methods of this type are typically employed where the non-conductive material substrate is supplied in a dry or molded form as a powder, pellet, tube or similar structure. The non-conductive material substrate is dissolved in a solvent or melted such that is becomes a liquid solution of the non-conductive material. In some cases, melting and solvent dissolution may be simultaneously employed in order to obtain a solution of the non-conductive material substrate.

When a solvent is used to dissolve a polymeric non-conductive material substrate, the resulting solution comprises a mixture of solvent and polymer. When melt processing is used, the non-conductive material substrate is simply melted to flow as a liquid.

The solvent used to dissolve the non-conductive material substrate is typically an organic solvent. Non-limiting examples of typical organic solvents include tetrahydrofuran, dimethyl sulfoxide, dichloromethane, chloroform, diethyl ether, acetone, methyl ethyl ketone, methanol, ethanol, isopropanol, n-butanol, water, toluene, heptane, hexane, benzonitrile, propylene carbonate and dimethylformamide.

After the non-conductive material is dissolved and/or melted to form a liquid substrate, the conductive monomer may be added directly to the liquid substrate to form a liquid composite solution.

The liquid composite solution can then be molded into a solid structure or, optionally, used to coat a scaffold or other underlying substrate. The scaffold or substrate may be dip coated or spray coated.

The molded structure or coating can then be dried to release any residual solvent.

If the conductive monomer has not yet been added to the solution of non-conductive material, it may be added to the dry non-conductive material substrate using an impregnation step, as described in detail herein.

The dry composite structure or liquid composite coating may then be subjected to a polymerization step to form an electrically conductive composite material. The polymerization step may comprise either oxidative polymerization or electrochemical polymerization, each of which may be carried out as described in detail herein.

The methods can be performed as a continuous process such as a continuous reel-to-reel chemical processing system wherein large amounts of conducting polymer-infused material can be produced.

Many types of non-conducting plastic tubing, fiber, and/or ribbon are available on rolls, or in other configurations that are amenable to continuous processing. Typically, one end of the material (e.g., on a first roll) can be unrolled and passed into a bath comprising the infusion medium as described above, through which the material slowly passes over the course of 10 minutes to several hours.

The monomer-impregnated material is then passed into a bath comprising an oxidizing medium as described above, which initiates polymerization of the conducting monomer to form the conducting polymer in situ.

The resulting electrically conductive composite material can then be passed through a rinsing or washing bath to remove any residual reagents.

A significant advantage of this process is that very long lengths of material can be continuously processed. These can then be stored for later use (e.g., on a second roll) or can be further processed for the desired application.

The processes and methods described herein enable the preparation of conductive structures and components for medical or other applications. For example, in the biomedical field, the composite materials described herein could form an implantable electrode in contact with tissue, an external electrode, connectors between the lead and implantable pulse generator or device header, or a lead cable or coil (connecting proximal and distal lead electrodes). These electrodes and components can be useful for cardiac pacing, cardiac defibrillation, cardiac sensing/electrogram recording (EKG), nerve/brain/spinal cord stimulation, nerve/brain/spinal cord sensing including ECoG/EEG, muscle stimulation, muscle sensing (EMG), wound healing, electrically-stimulated wound healing, tissue engineering, nerve grafts, electrically-stimulated reinnervation, vascular grafts, heart valves, drug delivery, antistatic agents, electromagnetic interference shielding, and grounding electrodes for ablation or surgical procedures.

Another aspect of the present invention is directed to a medical device comprising a composite material prepared in accordance with the methods set forth above. For example, the medical device can be an implantable medical device.

Additional uses of these composite materials include electrodes in batteries, fuel cells, and energy generating devices (such as piezoelectric devices). The process can be applied to various textiles, building materials, or other objects as components of organic photovoltaic generators, organic light-emitting devices, wearable electronics and other personal, health, or environmental sensors, for example. The composite materials also have antistatic properties that can be useful to protect people and delicate electronics.

For use as an X-ray contrast marker or as electromagnetic shielding, the composite materials can be filled with compounds that absorb various portions of the electromagnetic spectrum.

As used herein, the term "non-conductive material" refers to the starting material that is to be impregnated with an intrinsically conductive polymer via chemical oxidative or electrochemical polymerization. As described above, the methods described herein may be used to significantly increase electrical conductivity of the starting material.

Although the methods described herein are most typically applied to materials that are inherently insulating, it is not required that starting material is completely non-conductive.

Typically, the non-conductive material is a polymer. For example, the non-conductive material may be a plastic material.

Typically, the non-conductive material is swellable or similarly infusable.

Typically, the non-conductive material is porous. More typically, the conducting polymer is entrapped within the pores of the non-conductive material.

The non-conductive material may comprise a synthetic material, a natural material or a degradable material.

Non-limiting examples of non-conducting synthetic materials that can be used in accordance with the methods described herein include: polyethylene terephthalate (PET), high-density polyethylene (HDPE), low-density polyethylene (LDPE), ultra-high-molecular-weight polyethylene (UHMWPE), polycarbonate, polystyrene, acrylic, poly(methyl methacrylate) (PMMA), poly(2-hydroxyethyl methacrylate) (PHEMA), polyacrylamide, polyacrylic acid, thermoset polyurethane, thermoplastic polyurethane, polyurethane foam, polytetrafluoroethylene (PTFE), ePTFE (GORE-TEX), polydimethylsiloxane (PDMS), poly(lactic-co-glycolic acid) (PLGA), poly-L-lactide (PLLA), polyglycolic acid (PGA), polyether ether ketone (PEEK), isoprene, polyvinyl chloride (PVC), polyether block amide (PEBAX), silicone, polyaldehyde, polypropylene, nylon, polyester, polyamide, polyimide, polybutadiene, nitrile butadiene rubber (NBR), synthetic rubber, block copolymers, sulfonated block copolymers, sulfonated perfluorinated polymers, styrene-isoprene-butadiene-styrene (SIBS), polymer electrolyte membranes (PEM), and polyurea.

Functionalized derivatives of the non-conducting synthetic materials described above may also be used in accordance with the methods described herein. For example, sulfonated, carboxylated, phosphated, or hydroxylated derivatives of the non-conducting synthetic materials described above may be used.

Non-limiting examples of non-conducting natural materials that can be used in accordance with the methods described herein include: fibrin, collagen, cellulose, chitin/chitosan, alginate, carrageenan, silk, wool, a lignin, gelatin, cotton, keratin, natural rubber, and a poly(amino acid).

Non-limiting examples of non-conducting degradable polymers that can be used in accordance with the methods described herein include: polycaprolactone, polyglycolic acid, poly(lactic-co-glycolic acid) (PLGA), polylactic acid, a polyanhydride (e.g., poly(SA-HAD anhydride), poly(β-hydroxybutyrate), a poly(ortho-ester), and a polyiminocarbonate.

Mixtures and/or blends of the non-conductive materials thereof may also be used in accordance with the methods described herein.

The methods described herein may be utilized to impart electrical conductivity to non-conductive materials of any shape or geometry. Non-limiting examples of material geometries that are compatible with the methods described herein include: tubing, rods, fibers (nano, micro, macro), mesh, rings, solid 3D pieces, hollow 3D pieces, components, patches, sheets, sponges, adhesives, gels, foam, bags, balloons, injection-molded parts, extruded parts, particles, hook and loop fasteners (e.g. VELCRO fasteners), films, needles, microneedles, braids, weaves, and knits.

The non-conductive material can be entirely comprised of polymer or can consist essentially of one or more polymers (i.e., any non-polymeric component of the non-conductive material is compatible with the conducting monomer and other components used in making the composite).

As used herein, the term "conductive monomer" refers to a monomeric unit that can be polymerized to form an intrinsically conductive polymer.

Generally, conductive polymers comprise multiple conducting repeat units assembled into chains with conjugated alternating single and double carbon-carbon bonds. Conductive polymers are also sometimes referred to as inherently or intrinsically conducting polymers, electroactive polymers, or conjugated polymers. Conductive polymers are ideally suited for joining or interfacing electronic and ionic systems, because they are capable of conducting both electronic and ionic charge. Conductive polymers can also utilize highly effective and efficient charge storage and transfer mechanisms, similar to capacitors. Without being bound to a particular theory, it is believed that conductive polymers facilitate efficient charge transport through delocalized electrons across conjugated alternating double-single carbon-carbon bonds along the molecular backbone.

The conductive monomer can comprise acetylene, fluorene, para-phenylene, pyrene, pyrrole, carbazole, indole, phenyl azide, aniline, thiophene, pyridine, or a mixture or functionalized derivative thereof.

The conductive monomer can comprise 3,4-ethylenedioxythiophene (EDOT) or a functionalized derivative thereof. For example, the conductive monomer can comprise 3,4-ethylenedioxythiophene, hydroxymethyl-EDOT, EDOT-vinyl, EDOT-ether allyl, EDOT-COOH, EDOT-MeOH, EDOT-silane, EDOT-vinyl, EDOT-acrylate, EDOT-silane, EDOT-sulfonate, EDOT-amine, EDOT-amide, EDOT-thiol, ProDOT (3,4-Propylenedioxythiophene), 3,4-(2,2-Dimethylpropylenedioxy)thiophene, 3,4-(2',2'-Diethylpropylene)dioxythiophene, or dimerized or trimerized derivatives of EDOT, such as bi-EDOT or tri-EDOT. More typically, the functionalized derivative of 3,4-ethylenedioxythiophene is selected from the group consisting of hydroxymethyl-EDOT, EDOT-vinyl, EDOT-ether allyl, bis-EDOT, and EDOT-acrylate.

Alternatively, the conductive monomer can comprise functionalized derivative of 3,4-ethylenedioxythiophene (EDOT) selected from the group consisting of hydroxymethyl-EDOT, EDOT-vinyl, EDOT-ether allyl, and EDOT-acrylate. More typically, the conductive monomer can comprise a functionalized derivative of 3,4-ethylenedioxythiophene EDOT comprising an alkene functional group.

The conductive monomer can comprise a mixture of EDOT and a functionalized EDOT derivative. Typically, the molar ratio of EDOT to the functionalized EDOT derivative is from about 0.5:1 to about 10:1. More typically, the molar ratio of EDOT to the functionalized EDOT derivative is from about 0.5:1 to about 2:1.

The conductive monomer can comprise hexylthiophene or a functionalized derivative thereof. The conductive monomer can comprise 4-vinylpyridine. Further, the conductive monomer can comprise 3-methyl thiophene. The conductive monomer can comprise melanin.

EDOT is a highly typical monomer for use in accordance with the methods describe herein. Poly(3,4-ethylenedioxythiophene) (PEDOT), which is the conducting polymer based upon the EDOT monomer, exhibits high conductivity and excellent environmental stability.

Optionally, the infusion medium, polymerization medium, the oxidation medium or any of the mediums described herein may further comprise a solvent component comprising one or more solvents.

Non-limiting examples of suitable solvents include: dichloromethane, acetonitrile, dimethylsulfoxide, N,N-dimethylformamide, chloroform, tetrahydrofuran, isopropanol, methanol, ethanol, propylene carbonate, benzonitrile, acetone, methyl ethyl ketone, n-butanol, toluene, water, and a combination thereof.

Typically, the solvent component of the infusion medium or the polymerization medium comprises at least one polar solvent. For example, the solvent component may comprise a mixture of acetonitrile and dichloromethane. In these embodiments, the solvent component typically comprises a majority of acetonitrile, which is particularly effective at solubilizing polar compounds and/or salts, and a minority of dichloromethane, which is particularly effective at initiating swelling of the non-conductive material.

The solvent component of the infusion medium or the polymerization medium may be employed to aid in the swelling of the non-conductive material. When a solvent component is included to improve swelling, it is typically included in a small volumetric ratio with respect to the monomer, typically from about 1% to about 50%, or from about 5% to about 30%.

Typically, the solvent should be selected such that it strikes a balance between having a non-polar character sufficient to swell the non-conducting material substrate, while simultaneously having a polar character sufficient to solubilize oxidants, acid, base, and salts, which are usually polar or ionic and may need to carry a formal charge throughout the reaction without precipitating out of solution.

In some instances, the non-conductive material to be infused can be swollen to its intrinsic maximum capacity in the presence of the conducting monomer only, with no solvent component. For example, EDOT is a liquid at room temperature, and is able to swell most non-conductive plastics to a degree that permits infusion. The selection of a conductive monomer that is capable of swelling the material, without causing damage to the material or requiring the presence of a solvent component, is advantageous in that it allows for a high loading of the conductive monomer, corresponding to a high level of conductivity in the final composite product.

When larger volumetric ratios of solvent to monomer are necessary to swell the non-conductive material, the concentration of monomer in the infusion medium or polymerization medium decreases, resulting in a reduced loading of the conductive monomer and, subsequently, a lower level of conductivity in the final composite product.

Preferably, the infusion medium or polymerization medium comprises from about 0.1 to 100% (v/v) (preferably from about 70 to about 95% (v/v)) conducting monomer and from 0 to 99.9% (v/v) (preferably from about 5 to about 30% (v/v)) organic solvent. For example, the infusion medium can comprise EDOT and dichloromethane in an 80:20 volumetric ratio or the polymerization medium can comprise EDOT, dichloromethane and counterions.

The infusion medium may consist essentially of EDOT.

Solvents for the oxidation medium or polymerization medium should allow the oxidizer, as well as any counterions and/or additional components as described herein, to enter the monomer-impregnated material and react with the monomer. More particularly, the solvent should solubilize the conductive monomer, the oxidizer, and any counterions and/or additional components to a degree necessary for the polymerization reaction to occur.

On the other hand, appropriate solvents should not swell the monomer-impregnated material so much that the monomer diffuses out before the polymerization reaction is complete.

Non-limiting examples of suitable solvents to include in the oxidation medium or polymerization medium include: dichloromethane, acetonitrile, dimethylsulfoxide, N,N-dimethylformamide, chloroform, tetrahydrofuran, isopropanol, methanol, ethanol, propylene carbonate, or water.

Non-limiting examples of suitable oxidizers include benzoyl peroxide, hydrogen peroxide, iron (III) para-toluenesulfonate, iron (III) chloride, gold (III) chloride, iodine, and bromine. A typical oxidizer is benzoyl peroxide. Benzoyl peroxide exhibits good solubility in organic solvents, and penetrates well into most non-conductive polymeric materials.

Typically, the oxidation medium or polymerization medium further comprises a counterion component comprising one or more counterions.

Typically, the conductive polymers described herein are cationic. For example, the conductive polymer typically carries an average charge per repeat unit of from about +0.1 to about +1.0. More typically, the conductive polymer carries an average charge per repeat unit of from about +0.25 to about +0.5, and most typically an average charge per repeat unit of about +0.33.

As a result, the oxidation medium or polymerization medium typically comprises a counterion component comprising one or more counterions comprising a negatively charged functional group. Typically, the negatively charged functional group comprises a phosphate group, a phosphonate group, a sulfamate group, a carboxylate group, a sulfate group, a sulfonate group, or a combination thereof. Preferably, the negatively charged functional group comprises a phosphate group, a carboxylate group, a sulfate group, a sulfonate group, or a combination thereof. More preferably, the negatively charged functional group comprises a sulfonate group, a carboxylate group, or a combination thereof. Most preferably, the negatively charged functional group comprises a sulfonate group.

The counterion may be in the form of an acid or a salt. For example, the counterion may be in the form of a salt wherein the cation comprises an ammonium ion, an organic cation, an alkali metal cation, an alkaline earth metal cation, or a combination thereof. More typically, the cation can be lithium, sodium, potassium, calcium, magnesium, hydronium, ammonium, tetraethylammonium, tetrapropylammonium, tetrabutylammonium, or a combination thereof.

By way of non-limiting example, the counterion component can comprise polyvinyl sulfonate, polystyrene sulfonate, polyallyl sulfonate, polyethyl acrylate sulfonate, polybutyl acrylate sulfonate, polyacryl sulfonate, polymethacryl sulfonate, poly-2-acrylamide-2-methylpropane sulfonate, polyisoprene sulfonate, polyvinyl carboxylate, polystyrene carboxylate, polyallyl carboxylate, polyacryl carboxylate, polymethacryl carboxylate, poly-2-acrylamide-2-methylpropane carboxylate, polyisoprene carboxylate, a polyacrylate, a polyamino acid (e.g., a polyglutamate), polydopamine, sulfonated poly ether ether ketone (S-PEEK), a sulfonated polyurethane, or a mixture thereof. Monomers from which the above polymer electrolytes are derived would also be useful counter-ions such as for example, vinyl sulfonate, styrene sulfonate, allyl sulfonate, ethyl acrylate sulfonate, butyl acrylate sulfonate, acryl sulfonate, methacryl sulfonate, 2-acrylamide-2-methylpropane sulfonate, isoprene sulfonate, vinyl carboxylate, styrene carboxylate, allyl carboxylate, acryl carboxylate, methacryl carboxylate, 2-acrylamide-2-methylpropane carboxylate, isoprene carboxylate, an acrylate, an amino acid (e.g., glutamate), dopamine, a sulfonated ether ether ketone (S-EEK), a sulfonated urethane, or a mixture thereof.

More typically, the counterion component comprises sulfonic acid, fluorosulfonate, toluene sulfonate, taurine, anthraquinone sulfonate, vinyl sulfonate, 2-acrylamido-2-methyl-1-propanesulfonic acid, polystyrene sulfonate, polyvinyl sulfonate, sulfonated polytetrafluoroethylene, polyanetholesulfonic acid, a salt or functionalized derivative thereof, or a mixture thereof.

The counterion component can comprise polystyrene sulfonate (PSS), either alone or in combination with one or more additional species.

Also, the counterion component can comprise paratoluene sulfonate (pTS), 4-vinylbenzenesulfonate, vinyl sulfonate, a polymer thereof, or a combination thereof. The secondary counterion component can comprise sulfonated polytetrafluoroethylene (sold under the trade name NAFION).

The counterion component can comprise a block copolymer derived from polystyrene sulfonate and maleic anhydride (PSS-CoMA).

More typically, the counterion component can comprise para-toluenesulfonate (tosylate), trifluoromethanesulfonate (triflate), naphthalene sulfonate, camphor sulfonate, dodecylbenzene sulfonate benzene sulfonate, perchlorate, tetrafluoroborate, hexafluorophosphate, fluoride, chloride, bromide, iodide, or a mixture thereof.

The infusion medium, polymerization medium, and/or oxidation medium described above may each further comprise one or more additives to improve process stability.

For example, the oxidation medium may each comprise a surfactant component comprising one or more surfactants.

The surfactant component can comprise one or more nonionic, cationic, anionic, zwitterionic, amphoteric surfactants, or a combination thereof. Typically, the surfactant component comprises a nonionic surfactant.

The nonionic surfactant is typically selected from the group consisting of polaxamers, polyoxyethylene oleyl ethers, polysorbitan, and polyoxyethylene derivatives of sorbitan monolaurate.

For example, the nonionic surfactant can comprise a polyoxypropylene-polyoxyethylene polaxamer (sold under the trade name PLURONIC F-68).

The nonionic surfactant can comprise a polyoxyethylene glycol alkyl ether. For example, the nonionic surfactant can comprise polyethylene glycol octadecyl ether (sold under the trade name BRIJ 78).

The nonionic surfactant can comprise a polyoxyethylene derivative of sorbitan monolaurate. For example, the nonionic surfactant can comprise polyoxyethylene (60 or 80) sorbitan monolaurate (sold under the trade names TWEEN 60 and TWEEN 80).

The infusion medium, polymerization medium and/or oxidation medium may each comprise an antioxidant component comprising one or more antioxidants.

The non-conductive material may be infused with one or more additional components. Non-limiting examples of additional components include: crosslinkers, conductive additives, and radioopacity additives.

The additional components set forth herein may be incorporated during either the infusion step or the oxidation step described above. More particularly, the additional components set forth herein may be incorporated into the infusion medium, polymerization medium and/or the oxidation medium.

Alternatively, the additional components set forth herein may be infused into the non-conductive material in one or more additional process steps. The additional components are typically combined with one or more solvents, either to prepare a liquid solution (in the case where the additional component is a solid), or to enable swelling of the non-conductive material. Typical solvents for use with the present methods are described in detail above.

The non-conductive material may be infused with a crosslinking component.

The crosslinking component typically comprises a monomer functionalized with a group selected from silane, acrylate, methacrylate, epoxide, glycidyl ether, vinyl, allyl, azide, a derivative thereof, and a combination thereof.

For example, the crosslinking component can comprise a silane-functionalized monomer. Typically, the crosslinking monomer comprises a vinyl silane, an alkoxy silane, an ethoxy silane, an isocyanatosilane, or another functionalized crosslinkable silane, such as a hydroxy-functional, mercapto-functional or amino-functional silane. More typically, the crosslinking monomer is selected from the group consisting of vinyl trimethoxysilane (VTMS), (3-Aminopropyl) triethoxysilane (APTES), and a combination thereof.

The crosslinking component can comprise an acrylate-functionalized monomer. For example, the crosslinking component can comprise an acrylate-functionalized monomer selected from the group consisting of ethylene glycol di-acrylate (EGDA), poly(ethylene glycol di-acrylate) (PEDGA), ethylene glycol dimethacrylate (EGDMA), poly (ethylene glycol dimethacrylate) (PEGDMA), and a combination thereof.

The non-conductive material may be infused with one or more additives that increase radioopacity. Non-limiting examples of radioopacity additives include heavy elements such as tantalum, platinum, and iridium.

The non-conductive material may be infused with one or more conductive additives. Non-limiting examples of conductive additives include carbon black, carbon fiber, pre-polymerized conducting polymers (e.g., PEDOT), carbon nanotubes, graphite, graphene, and metal particles and/or powders, including nickel, platinum, gold, silver, iridium, tantalum, cobalt, chromium, titanium, stainless steel, and mixtures or alloys thereof (e.g., MP35N). Another aspect of the present disclosure is directed to a composite material comprising a non-conductive material impregnated with a conducting polymer, the composite material being prepared by any of the processes or methods described above.

The composite material can comprise a conducting polymer entrapped within a non-conductive material.

The composite material can comprise a non-conductive material containing a conducting polymer entrapped therein and having at least one surface coated with the conducting polymer. For example, the conducting polymer can coat the exterior of the non-conductive material as well as being entrapped in the interior of the non-conductive material. The non-conductive material is as described herein.

The conducting polymer may comprise a polyacetylene, a poly(fluorene), a polyphenylene, a polyphenylene vinylene, a polypyrene, a polyazulene, a polynaphthalene, a poly (pyrrole), a polycarbazole, a polyindole, a polyazepine, a polyaniline, a polyacene, a polythiophene, a polythiophene vinylene, a poly(p-phenylene sulfide), a polypyridine, or functionalized derivatives, precursors or blends thereof.

Typically, the conducting polymer comprises poly(3,4-ethylenedioxythiophene) (PEDOT) or a functionalized derivative thereof. For example, the conducting polymer may be derived from a functionalized derivative of EDOT selected from the group consisting of hydroxymethyl-EDOT, EDOT-vinyl, EDOT-ether allyl, or EDOT-acrylate.

The conducting polymer can comprise poly(hexylthiophene), or a salt or functionalized derivative thereof; poly-4-vinylpyridine, or poly(diallyldimethylammonium chloride).

The composite material can comprise a conducting polymer that was formed by polymerization in situ.

Having described the invention in detail, it will be apparent that modifications and variations are possible without departing from the scope of the invention defined in the appended claims.

EXAMPLES

The following non-limiting examples are provided to further illustrate the present invention.

Example 1

Preparation of Electrically Conductive Composite Material Using Chemical Oxidative Polymerization A roll of non-conductive, medical grade thermoplastic polyurethane 2363-55D tubing, having an inner diameter of 0.042" and an outer diameter of 0.054", was cut into three one-inch sections. Combined mass of pristine tubes was measured to be 0.050 g.

The polyurethane 2363-55D sections were then submerged in a liquid solution of 3,4-ethylenedioxythiophene (EDOT) monomer and dichloromethane in an 80:20 volumetric ratio. The sections were allowed to soak for 24 hours at room temperature. The tubes were massed a second time and it was determined that combined they absorbed 0.141 g EDOT monomer.

Separately, an oxidation medium was prepared. 0.100 g para-toluenesulfonic acid monohydrate (HpTS; 98.5% purity) and 0.40 g lithium trifluoromethanesulfonate (96% purity) were dissolved into 5 mL of acetonitrile (ACN). Once the solids were dissolved, 5 mL of dichloromethane was added. Next 0.240 g benzoyl peroxide (BP)(98% purity) was added to the solution. 0.240 BP was calculated as the necessary oxidant required because it is in a 1:1 molar ratio with the 0.141 g EDOT monomer absorbed by the polyurethane tubes. The monomer impregnated polyurethane tubes were next transferred to the freshly prepared oxidation solution described above. The polymerization reaction proceeds for about 20 hours at about 37° C. on a shaker plate at about 200 RPM. Shaking helps keep the solution well mixed and helps prevent a gradient from forming due to precipitating PEDOT. This not only improves conductivity, but also maintains uniformity across the length of the tubes. Following the oxidation step, the resulting electrically conductive, composite structures were rinsed in a mixture of water and organic solvent, and were inserted into a chamber under vacuum to remove any residual processing chemicals or solvents.

Example 2

Preparation of Electrically Conductive Composite Material Using Electrochemical Polymerization in Monomer Infused Substrate As a variation of the method described above in Example 1, the conductive monomer was polymerized in situ using an electrochemical polymerization step, rather than oxidative chemical polymerization.

After soaking for 24 hours in the monomeric solution as described above, a section of the polyurethane 2363-55D tubing was connected to a rod-shaped working electrode that was inserted into the lumen of the tubing. This complex was then inserted into a beaker containing an electrochemical deposition solution comprised of acetonitrile and 0.1 M lithium triflate counter-ion. The electrochemical cell was completed by immersing a platinum mesh counter electrode opposite the substrate to be impregnated with PEDOT. Current was then applied between the working and counter electrode at a current density across the working electrode of 0.1 mA/cm$^2$ to 10.0 mA/cm$^2$ for several minutes.

Example 3

Preparation of Electrically Conductive Composite Material Using a Single-Step Chemical Oxidative Polymerization A section of polyurethane foam is cut to 1 inch×1 inch× 0.25 inch. A reaction solution is prepared by dissolving 0.500 g para-toluenesulfonic acid monohydrate (HpTS) (98.5% purity) and 2.00 g lithium trifluoromethanesulfonate (LiTriflate) (96% purity) in 50 mL propylene carbonate.

After all solids are dissolved 0.341 g benzoyl peroxide (BP) (98% purity) is added to the reaction solution. After all solids have dissolved 0.200 g (150 uL) EDOT monomer is pipetted into the reaction solution. 0.200 g EDOT is used because it is in a 1:1 molar ratio with 0.341 g benzoyl peroxide. EDOT monomer is stirred in and the polyurethane foam cut sample is immediately added. The substrate is immersed in solution immediately following addition of the monomer because the reaction has begun. The reaction proceeds at about 37° C. on a shaker plate at about 200 RPM for about 20 hours. Shaking improves mixing and prevents a gradient from forming due to precipitating PEDOT. It improves conductivity as well as uniformity. Agitation also reduces particulate which results in a cleaner final product. Next the conductive composite polyurethane foam is washed in water and an organic solvent to remove residual chemicals and any weakly adhering PEDOT.

Example 4

Preparation of Electrically Conductive Composite Material Using Electrochemical Polymerization in a Single Step As a variation of the method described above in Example 2, the conductive monomer was polymerized in situ using an electrochemical polymerization step without an initial monomer infusion step. In this variation the monomer infuses during the polymerization step.

Polyurethane 2363-55D is dissolved in tetrahydrofuran solution at 10% w/v. A section of 18 gauge stainless steel 316L hypotube is dipped into the polymer solution and allowed to dry at 50° C. for 30 minutes. The result is a Pellethane 2363-55D coated length of stainless steel hypotube. A deposition solution comprised of acetonitrile, 0.10 M EDOT monomer, and 0.10 M lithium triflate counter-ion is prepared. An electrochemical cell is prepared for electrochemical deposition by submerging the Pellethane coated portion of the hypotube in the deposition solution, this is the working electrode and anode. A platinum mesh counter electrode is submerged opposite the working electrode and acts as the cathode. Ideally the hypotube is positioned vertically in the deposition solution and the counter electrode is surrounding the submerged portion of the hypotube in a concentric circle spaced equidistant from the hypotube at all regions around its circumference. An anodic current is passed through this two-electrode electrochemical cell with a current density of 0.10 mA/cm2 to 100.0 mA/cm2 across the working electrode for 1 second-10 hours, more preferably at a current density of 0.5 mA/cm2 to 5 mA/cm2 for 5-20 minutes.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there can be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A method of making a composite material, the method comprising:
    soaking a non-conductive material in an infusion medium comprising an organic solvent capable of swelling the non-conductive material;
    during or after the immersing step, impregnating the non-conductive material with a conducting monomer to form a monomer-impregnated non-conductive material; and
    polymerizing the monomer-impregnated non-conductive material to form the composite material,
    wherein the composite material has greater conductivity as compared to the non-conductive material impregnated with the conducting monomer without soaking in the infusion medium, wherein the polymerizing step comprises
        electrochemically polymerizing the monomer within the monomer-impregnated non-conductive material by placing the monomer-impregnated non-conductive material in a deposition medium containing counter-ions and a solvent and applying a current.

2. The method of claim 1, wherein the impregnating step comprises soaking the non-conductive material in the infusion medium comprising the conducting monomer and the organic solvent to form the monomer-impregnated non-conductive material.

3. The method of claim 2, wherein the infusion medium comprises from about 50 to 90% v/v conducting monomer and from 10 to about 50% v/v organic solvent.

4. The method of claim 3, wherein the impregnating step occurs for about 15 minutes to about 250 hours at about 0° C. to about 120° C.

5. The method of claim 4, wherein the impregnating step occurs for about 12 hours to about 36 hours at about 20 to 40° C.

6. The method of claim 1, wherein
    the impregnating step comprises delivering a gas containing the conducting monomer or a liquid containing the conducting monomer into a sealed chamber containing the non-conductive material to form the monomer-impregnated non-conductive material; and/or
    the polymerizing step comprises delivering a gas containing the oxidizer or a liquid containing the oxidizer into a sealed chamber containing the monomer-impregnated non-conductive material to form the composite material.

7. The method of claim 6, wherein the chamber is at a pressure below atmospheric pressure to increase the porosity of the non-conductive material.

8. The method of claim 1, wherein the non-conductive material is impregnated and the monomer-impregnated non-conductive material is polymerized in a single step reaction.

9. The method of claim 8 wherein an oxidation medium contains the conducting monomer, a solvent, and an oxidizer such that the conducting monomer and the oxidizer react and the conducting monomer is polymerized to form the composite material.

10. The method of claim 1, wherein the non-conductive material or substrate comprises a tube, scaffold, rod, fiber, mesh, ring, patch, sheet, sponge, gel, foam, bag, balloon, particle, powder, pellet, hook and loop fastener, film, needle, braid, weaved material, knitted material, extruded material, or injection-molded material.

11. The method of claim 1, wherein the method further comprises electrochemically depositing a conductive polymer on a surface of the composite material.

12. The method of claim 1, wherein the conducting monomer comprises acetylene, fluorene, para-phenylene, pyrene, pyrrole, carbazole, indole, phenyl azide, aniline, thiophene, pyridine, or a mixture or functionalized derivative thereof;
  the conducting monomer comprises 3,4-ethylenedioxythiophene (EDOT) or a functionalized derivative thereof; the conducting monomer comprises 3,4-ethylenedioxythiophene, hydroxymethyl-EDOT, EDOT-vinyl, EDOT-ether allyl, EDOT-COOH, EDOT-MeOH, EDOT-silane, EDOT-vinyl, EDOT-acrylate, EDOT-silane, EDOT-sulfonate, EDOT-amine, EDOT-amide, EDOT-thiol, ProDOT (3,4-Propylenedioxythiophene), 3,4-(2,2-Dimethylpropylenedioxy)thiophene, 3,4-(2', 2'-Diethylpropylene)dioxythiophene, or a dimerized or trimerized derivative of EDOT; or the conducting monomer comprises hydroxymethyl-EDOT, EDOT-vinyl, EDOT-ether allyl, or EDOT-acrylate.

13. The method of claim 1, wherein the non-conductive material comprises a plastic; a synthetic material comprising polyethylene terephthalate (PET), high-density polyethylene (HDPE), low-density polyethylene (LDPE), ultra-high-molecular-weight polyethylene (UHMWPE), polycarbonate, polystyrene, poly(methyl methacrylate) (PMMA), poly(2-hydroxyethyl methacrylate) (PHEMA), polyacrylamide, polyacrylic acid, thermoset polyurethane, thermoplastic polyurethane, polyurethane foam, polytetrafluoroethylene (PTFE), ePTFE (GORE-TEX), polydimethylsiloxane (PDMS), poly(lactic-co-glycolic acid) (PLGA), poly-L-lactide (PLLA), polyglycolic acid (PGA), polyether ether ketone (PEEK), isoprene, polyvinyl chloride (PVC), polyether block amide (PEBAX), silicone, polyaldehyde, polypropylene, polybutadiene, styrene-isoprene-butadiene-styrene (SIBS), block copolymers, sulfonated block copolymers, sulfonated perfluoronated polymers, polymer electrolyte membranes (PEM), nitrile butadiene rubber (NBR), synthetic rubber, nylon, polyester, polyamide, polyimide, polyurea, or a functionalized derivative thereof; a natural material comprising fibrin, collagen, cellulose, chitin/chitosan, alginate, carrageenan, silk, wool, lignin, gelatin, cotton, keratin, natural rubber, or a poly(amino acid); or
  a degradable material comprising polycaprolactone, polyglycolic acid, poly(lactic-co-glycolic acid) (PLGA), polylactic acid, a polyanhydride, poly((3-hydroxybutyrate), a poly(ortho-ester), or a polyiminocarbonate.

14. The method of claim 1, wherein the non-conductive material is impregnated with the conducting monomer and a crosslinking agent to form the monomer-impregnated non-conductive material; or the monomer-impregnated non-conductive material is in the presence of a crosslinking agent during polymerization.

15. The method of claim 14, wherein the crosslinking agent comprises a monomer functionalized with a silane, an acrylate, a methacrylate, epoxide, glycidyl ether, vinyl, allyl, azide, a derivative thereof, or a combination thereof.

* * * * *